United States Patent
Oktavec et al.

(10) Patent No.: US 9,060,878 B2
(45) Date of Patent: Jun. 23, 2015

(54) PERCUTANEOUS BIOLOGIC DELIVERY SYSTEM

(76) Inventors: Ray G. Oktavec, West Palm Beach, FL (US); Thomas F. Roush, West Palm Beach, FL (US)

( * ) Notice: Subject to any disclaimer, the term of this patent is extended or adjusted under 35 U.S.C. 154(b) by 378 days.

(21) Appl. No.: 13/433,216

(22) Filed: Mar. 28, 2012

(65) Prior Publication Data

US 2012/0253316 A1 Oct. 4, 2012

Related U.S. Application Data

(60) Provisional application No. 61/468,454, filed on Mar. 28, 2011.

(51) Int. Cl.
| | |
|---|---|
| A61M 29/02 | (2006.01) |
| A61F 2/46 | (2006.01) |
| A61B 17/34 | (2006.01) |
| A61B 17/17 | (2006.01) |
| A61M 29/00 | (2006.01) |
| A61B 17/16 | (2006.01) |
| A61B 17/00 | (2006.01) |

(52) U.S. Cl.
CPC ........... *A61F 2/4601* (2013.01); *A61B 17/3472* (2013.01); *A61M 29/00* (2013.01); *A61B 17/1671* (2013.01); *A61B 17/1757* (2013.01); *A61B 17/3421* (2013.01); *A61B 2017/0046* (2013.01); *A61B 2017/00477* (2013.01); *A61B 17/1635* (2013.01)

(58) Field of Classification Search
CPC ........... A61B 17/3472; A61B 17/1635; A61B 17/1371; A61B 17/1757; A61B 17/3421
USPC ....................................................... 606/92, 93
See application file for complete search history.

(56) References Cited

U.S. PATENT DOCUMENTS

| | | | |
|---|---|---|---|
| 5,762,629 A | 6/1998 | Kambin | |
| 6,395,007 B1 | 5/2002 | Bhatnagar et al. | |
| 6,613,054 B2 * | 9/2003 | Scribner et al. ................. | 606/93 |
| 7,198,598 B2 | 4/2007 | Smith et al. | |
| 7,556,650 B2 | 7/2009 | Collins et al. | |
| 2004/0176763 A1 | 9/2004 | Foley et al. | |
| 2006/0004326 A1 | 1/2006 | Collins et al. | |
| 2009/0157085 A1 | 6/2009 | Melsheimer | |
| 2009/0187194 A1 | 7/2009 | Hamada | |

(Continued)

FOREIGN PATENT DOCUMENTS

| | | |
|---|---|---|
| WO | 0054705 | 9/2000 |
| WO | 03020137 | 3/2003 |

(Continued)

*Primary Examiner* — Laura Bouchelle

(74) *Attorney, Agent, or Firm* — Akerman LLP; Peter A. Chiabotti

(57) ABSTRACT

A bone grafting delivery device, method and kit is provided. The bone grafting material delivery device may include a needle having a cutting edge located at a distal end of the needle. The needle may be configured to be inserted within a bone via an entry point created through the skin of a patient. Additionally, the bone grafting material delivery device may include a plurality of dilators attachable sequentially to the needle using a swivel assembly. The plurality of dilators may be configured to articulate relative to needle in a plurality of directions via the swivel assembly. Furthermore, a final dilator of the plurality of dilators may include an opening at a distal end of the final dilator for depositing bone grafting material onto the bone or in a void.

11 Claims, 18 Drawing Sheets

(56) References Cited

U.S. PATENT DOCUMENTS

2010/0004655 A1   1/2010   Choi
2010/0069912 A1   3/2010   Mccormack et al.

FOREIGN PATENT DOCUMENTS

WO   2004037074   5/2004
WO   2008097659   8/2008

* cited by examiner

PERCUTANEOUS BIOLOGIC DELIVERY SYSTEM

RELATED APPLICATIONS AND PRIORITY

The present application claims priority to U.S. Provisional Application No. 61/468,454, filed Mar. 28, 2011, the entirety of which is hereby incorporated by reference.

FIELD OF THE INVENTION

The present application relates to medical devices and instruments related to bone grafting, and, more particularly, to a percutaneous biologic delivery system.

BACKGROUND

Advances in medical devices, technology, and techniques have greatly increased patient standard of living and survival rates, while also reducing complications. However, further advances are desired to minimize the invasive nature of some of these devices and techniques, which may on occasion cause preventable collateral tissue, bone, or other damage during a medical procedure. Back surgeries such as spinal fusions, discectomies, foramenotomies, laminectomies, and spinal disc replacements are often quite invasive and may potentially have undesirable consequences such as, but not limited to, failed back syndrome, which can cause tremendous pain for patients. Additionally, as the number of complex back surgeries being performed continues to increase each year, the risk of life threatening complications may increase significantly as well. As a result, medical costs, hospital visits, unnecessary additional medical procedures, and other undesirable consequences may rise considerably. Such consequences can place considerable pressure on an already taxed medical system. Therefore, providing surgical options that help to curb such adverse consequences that also provide better devices and methods for performing the surgeries, is desirable.

SUMMARY

A bone grafting material delivery device, method, and kit are disclosed, along with an assembly for detachably coupling minimally invasive instruments and method a accessing a surgical area through a minimally invasive channel. The bone grafting material delivery device may be utilized in an operating room during various different types of surgeries. For example, the bone grafting material delivery device may be utilized during spinal fusion surgery, which is one of the most common surgeries performed on the spine today. It is estimated that over 400,000 of these types of surgeries are performed worldwide each year. Notably, spinal fusion surgeries require the use of bone grafting material to effectively fuse vertebrae together. The bone grafting material delivery devices and methods disclosed herein provide for percutaneous bone grafting by delivering bone grafting material to a precise area to various elements of a patient's spine and by effectively decorticating selected bones of the patient with minimal invasiveness. Specifically, the bone grafting material delivery device may dock to an element of a patient's spine, decorticate the spine, dilate the relevant surgical area, and provide for directional control when depositing the bone grafting material on a bone or in a void.

In particular, the bone grafting material delivery device may include a needle for docking the bone grafting material delivery device into a bone of a patient during a particular procedure. One or more dilators may be sequentially attached to a portion of the needle and may be advanced down to the location where the needle is anchored to the bone. A final dilator of the dilators may have an opening through which bone grafting material may be deposited. The location where the needle meets the bone may be the location where a surgeon or other individual deposits the bone grafting material via the opening of the final dilator. The bone grafting material may be directionally deposited onto the bone or a void by utilizing an articulation joint or a swivel assembly of the bone grafting material delivery device to move the final dilator in a plurality of directions.

In one embodiment, a bone grafting material delivery device may be provided. The bone grafting material delivery device may include a needle having a groove and a cutting edge located at a distal end of the needle. The needle may be configured to anchor to a location in a bone via a skin entry point created on a patient. Additionally, the bone grafting material delivery device may include a plurality of dilators attachable sequentially to the groove of the needle. In another embodiment, a swivel assembly, that may include a dilator ring, a knob assembly, a stud, a lock lever, and a clamp assembly, can be provided to detachably couple one or more dilators to the needle. The plurality of dilators may be configured to articulate relative to the needle in a plurality of directions via an articulation joint. Furthermore, a final dilator of the plurality of dilators may include an opening at a distal end of the final dilator for depositing bone grafting material onto the bone, in a void, or a combination thereof.

In another embodiment, a method for allowing preparation of a fusion bed via decortication or delivering bone grafting material may be provided. The method may include determining a location on a body of a patient for creating an entry point to deliver the bone grafting material. Also, the method may include creating the entry point at the location on the body of the patient and positioning a needle in a bone of the patient via the entry point. The method may additionally include attaching sequentially a plurality of dilators to a portion of the needle. The plurality of dilators may be configured to articulate from the needle in a plurality of directions via an articulation joint. A final dilator of the plurality of dilators may include an opening at a distal end of the final dilator. The method may further include depositing the bone grafting material via the opening of the final dilator onto or in at least one of the bone of the patient or a void.

In another embodiment, a bone grafting material delivery device kit may be provided. The bone grafting material delivery kit may include a needle having a cutting edge and at least one groove positioned along a surface of the needle. Additionally, the bone grafting material delivery kit may include one or more dilators configured to be attached to the needle via the groove of the needle. The one or more dilators may configured to articulate from the needle in a plurality of directions. Moreover, the bone grafting material delivery kit may include a final dilator configured to be attached to the needle via the groove of the needle. The final dilator may include an opening at a distal end of the final dilator for depositing bone grafting material onto a bone, in a void, or a combination thereof.

According to another exemplary embodiment, another bone grafting material delivery device may be provided. The bone grafting material delivery device may include a needle having a cutting edge located at a distal end of the needle. The needle may be configured to anchor to a location in a bone via a skin entry point created on a patient. Additionally, the bone grafting material delivery device may include a plurality of dilators attachable sequentially to the needle using a swivel assembly. The plurality of dilators may be configured to articulate relative to the needle in a plurality of directions via the swivel assembly. Furthermore, a final dilator of the plurality of dilators may include an opening at a distal end of the final dilator for depositing bone grafting material onto the bone, in a void, or a combination thereof.

In another embodiment, a method for accessing a surgical area through a minimally invasive channel may be provided. The method may include determining a location on a body of a patient for creating an entry point to deliver the bone grafting material. Also, the method may include creating the entry point at the location on the body of the patient and positioning a needle in a bone of the patient via the entry point. The method may additionally include attaching sequentially a plurality of dilators to a portion of the needle by using a swivel assembly. The plurality of dilators may be configured to articulate from the needle in a plurality of directions via the swivel assembly. A final dilator of the plurality of dilators may include an opening at a distal end of the final dilator. The method may further include depositing the bone grafting material via the opening of the final dilator onto or in at least one of the bone of the patient or a void.

In still another embodiment, a bone grafting material delivery device kit may be provided. The bone grafting material delivery kit may include a needle having a cutting edge and one or more dilators configured to be attached to the needle via a swivel assembly. Additional instruments for fusion preparation of a surface, such as a burr, can also be included. The one or more dilators may be configured to articulate from the needle in a plurality of directions. Moreover, the bone grafting material delivery kit may include a final dilator configured to be attached to the needle via swivel assembly. The final dilator may include an opening at a distal end of the final dilator for depositing bone grafting material onto a bone, in a void, or a combination thereof.

These and other features of the are described in the following detailed description, drawings, and appended claims.

DETAILED DESCRIPTION OF THE INVENTION

Figure 1:
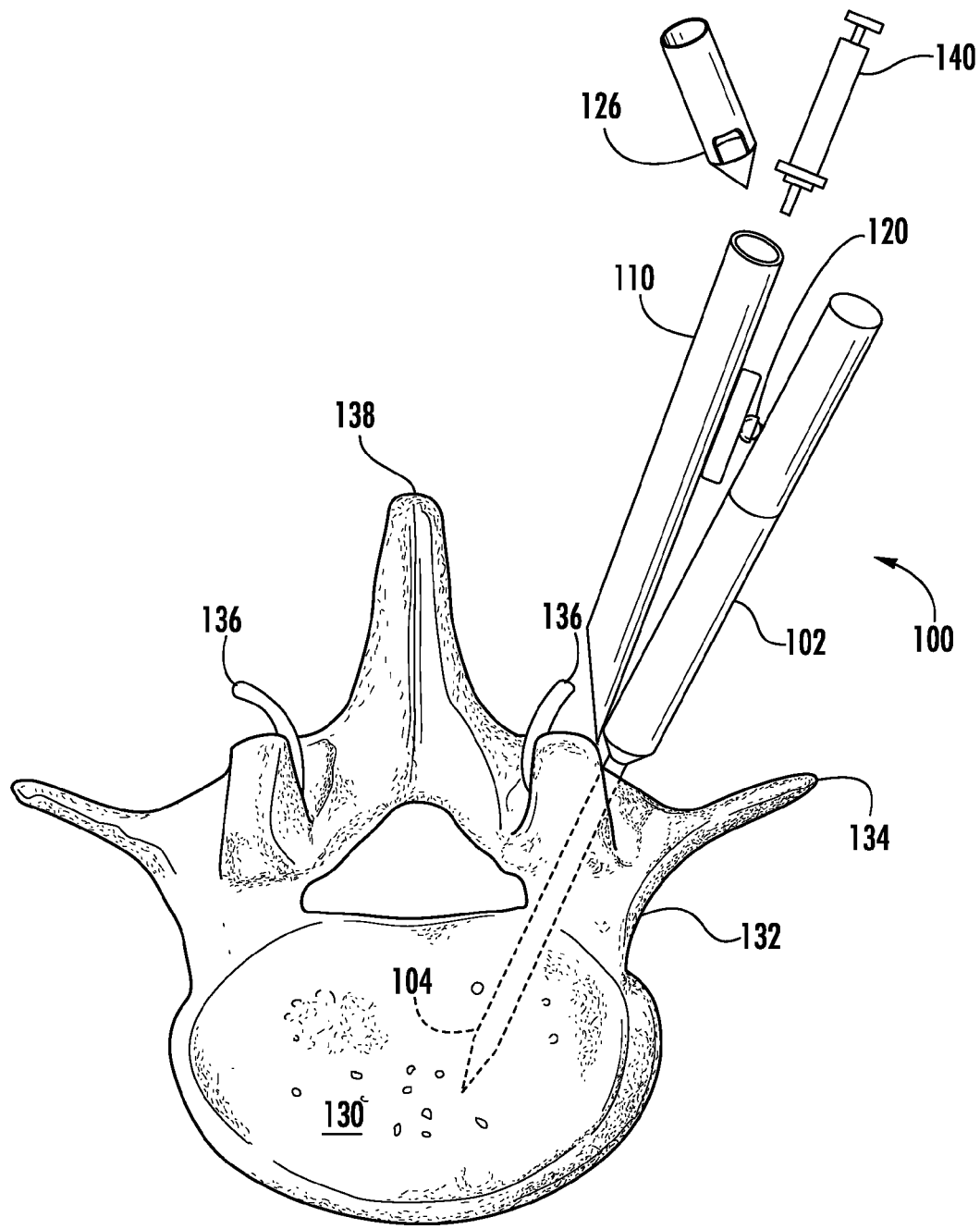
FIG. 1 is a perspective view of the bone grafting material delivery device according to an exemplary embodiment.
Figure 2:
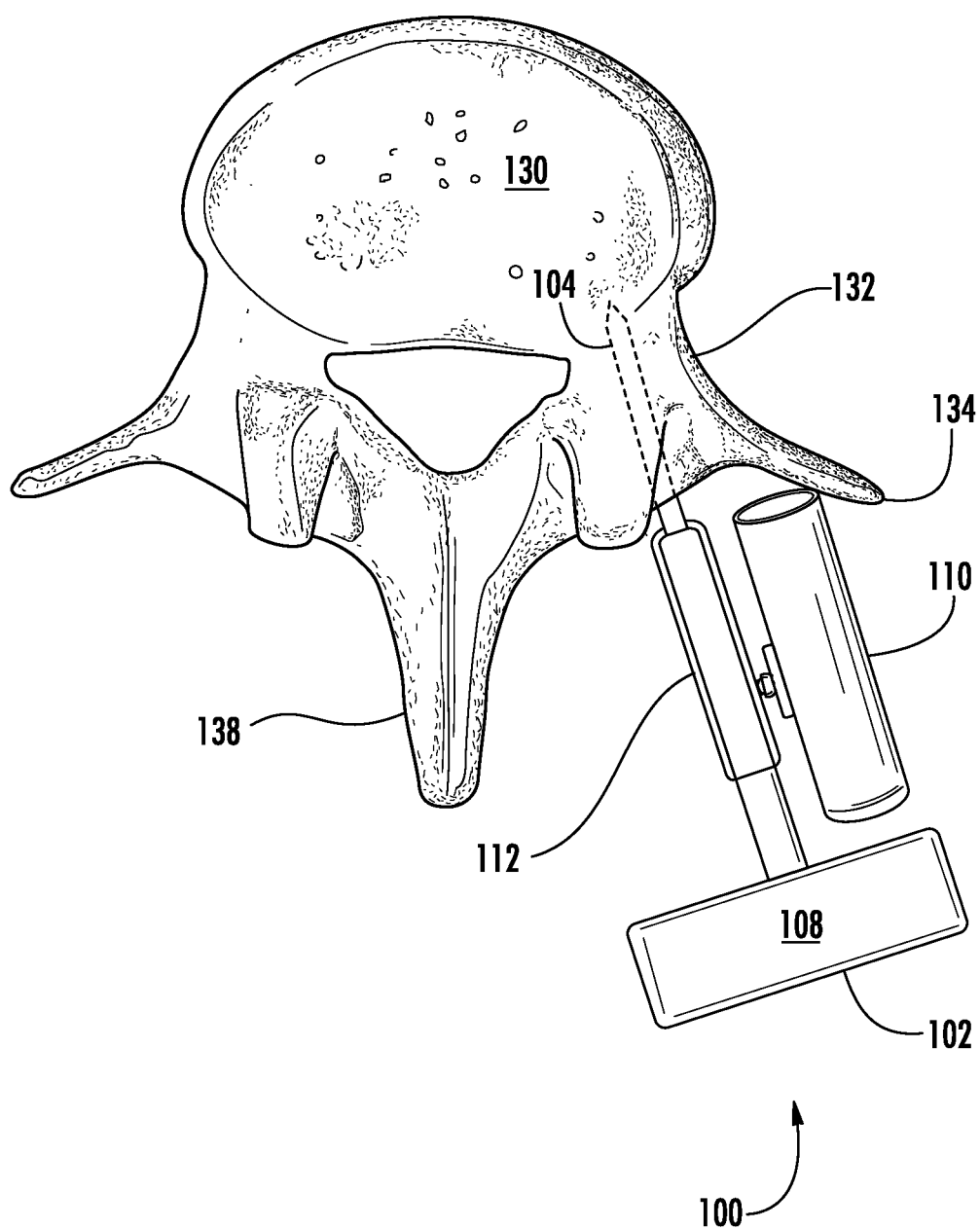
FIG. 2 is another perspective view of the bone grafting material delivery device.

The exemplary embodiments of the present disclosure are described with respect to bone grafting delivery devices, corresponding kits, and methods for delivering bone grafting material utilizing the bone grafting delivery devices. In an embodiment, the bone grafting material delivery device may include a needle for docking the bone grafting material delivery device onto a bone of a patient during a surgical procedure. For example, the bone grafting delivery device may be utilized during a spinal fusion surgery or other similar surgeries. One or more dilators may be sequentially attached to a groove of the needle and the dilators may be advanced down to the location where the needle meets the bone. However, the dilators do not necessarily have to be sequentially attached and, instead, may be attached in a variety of different manners. A final dilator of the dilators may be attached to the needle and may have an opening through which bone grafting material may be deposited. The bone grafting material may be directionally deposited onto the bone or in a void proximate to the bone by depositing the bone grafting material or any other biologics via the opening of the final dilator and adjusting a position of the final dilator.

In another embodiment, another bone grafting material delivery device may be provided. The bone grafting material delivery device may include a needle for docking the bone grafting material delivery device onto a bone of a patient. However, in this embodiment, the one or more dilators may be attached to the needle by utilizing a swivel assembly, which may allow the dilators to articulate relative to the needle in a variety of directions such that bone grafting material may be deposited in a variety of locations. The swivel assembly may include a clamp, which may be configured to receive at least a portion of the needle so that the swivel assembly may be secured to the needle. Additionally, the swivel assembly may include a lock lever that may enable the dilators to be fixed in a desired position for depositing the bone grafting material effectively. A final dilator of the dilators may be attached to the swivel assembly and needle and may include an opening through which the bone graft material may be delivered to the intended location.

Referring to the drawings and in particular to FIGS. 1-6, a bone grafting material delivery device 100 according to one embodiment of the invention is schematically illustrated. The bone grafting material delivery device 100 may include a needle 102, one or more dilators 110, and a final dilator 116. Notably, the one or more dilators 110 and the final dilator 116 may be attached in sequence to a groove 106 of the needle 102 via an attachment structure 112. However, the dilators 110 and the final dilator 116 do not necessary have to be sequentially attached. Instead, the dilators 110 and the final dilator 116 may be attached in various other manners. The dilators 110 and the final dilator 116 can move in a variety of directions with respect to the needle 102 based on an articulation joint 120 of the attachment structure 112. The bone grafting material delivery device may also include a syringe 140, which may be utilized to push the bone grafting material through the final dilator 116 onto a bone or in a void proximate to the bone of the patient. The bone grafting material may include, but is not limited to including, at least one of an autograph, recycled bone, calcium phosphate, a synthetic, a biologic, or a combination thereof.

Figure 3:
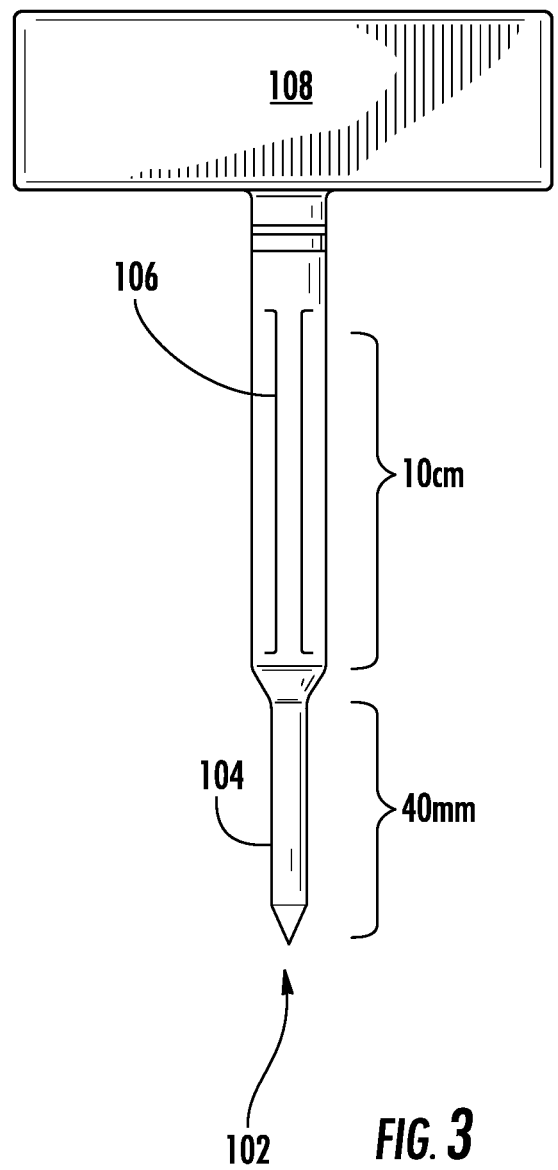
FIG. 3 is a needle for use with a bone grafting material delivery device according to an embodiment.
Figure 4:
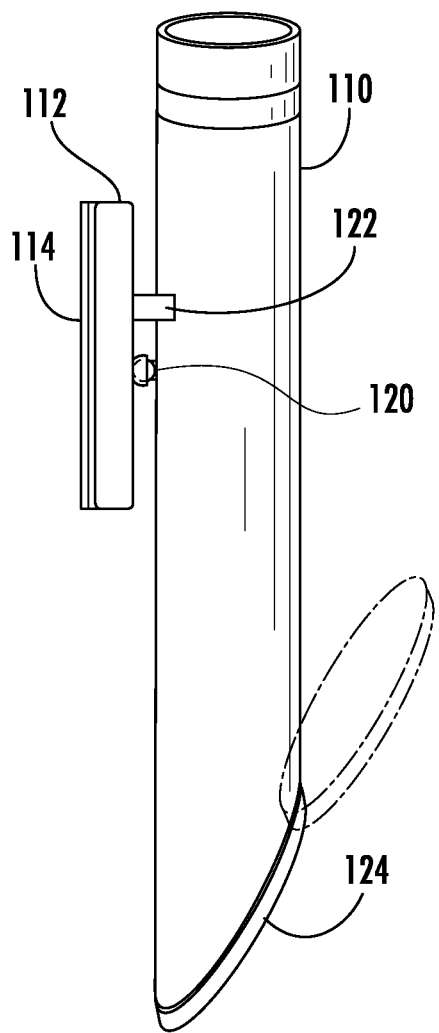
FIG. 4 is a dilator including an attachment structure and articulation joint to be utilized with the bone grafting material delivery device.
Figure 5:
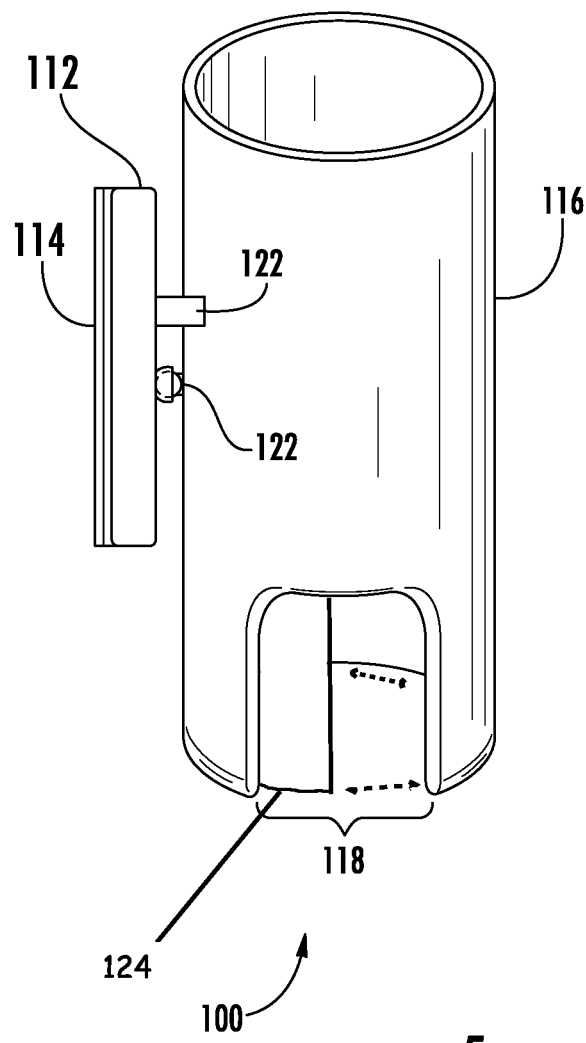
FIG. 5 is a schematic illustration depicting a final dilator attached to the attachment structure of the bone grafting material delivery device.
Figure 6:
FIG. 6 is another schematic illustration of the bone grafting material delivery device.

In more specific detail, the needle 102 of the bone grafting material delivery device 100, in an embodiment, may be a Jamshidi needle or other suitable needle. The needle 102 may be formed of steel, plastics, metals, or other suitable materials, and may be constructed for a single use or for multiple uses after being appropriately sterilized. The needle 102 may include a cutting edge 104 that may be utilized to cut into a bone of an individual and, as a result, enable the needle 102 to anchor into the bone. In an embodiment, the cutting edge 104 may be approximately forty millimeters in length. Additionally, the needle 102 may include a groove 106 that may be positioned at various locations on the body of the needle 102. For example, as illustrated in FIG. 3, the groove 106 may be along a shaft portion of the needle 102. The groove 106 can extend parallel to the longitudinal axis of the needle 102. Additionally, the needle 102 can include more than one groove 106. In an embodiment, the needle 102 may include markers of an appropriate distance (e.g. 10 cm) that are positioned proximate to the groove 106. Notably, however, the groove 106 may be positioned along other portions of the needle 102 as well.

Also, the needle 102 may include a detachable or removable handle 108 at a proximal end of the needle 102. The removable handle 108 may screw into the proximal end, snap into the proximal end, or otherwise fasten or connect to the proximal end of the needle 102. Additionally, the removable handle 108 may include grooves to allow an individual to grip the removable handle 108. The removable handle 108 may allow a surgeon or other medical professional to easily hold the needle 102 so that it may be more readily anchored into a bone of a patient.

The one or more dilators 110 of the bone grafting material delivery device 100 may be utilized to dilate a surgical area of the patient and to deliver the bone grafting material to a bone and/or in a void area of a patient. The dilators 110 may be made of suitable materials such as plastics, metals, or other suitable materials and may have varying lengths, heights, widths, and circumferences. In an embodiment, the measurements of the dilators 110 may commonly vary between 1-2 cm in diameter, with the lengths of the dilators 110 varying from 5-15 cm. Additionally, in an embodiment, the shapes of the dilators 110 may be cylindrical. However, other shapes are contemplated as well. Furthermore, the dilators 110 may be for single or multiple use. Each dilator 110 may be connected to the groove 106 of the needle 102 by utilizing an attachment structure 112. The attachment structure 112 may include male grooves 114 that are designed to securely connect to the groove 106 of the needles 102. Specifically, the male grooves 114 may be configured to slide into the groove 106, snap into the groove 106, or otherwise connect to the groove 106. Each dilator 110 may be interchanged such that they are used in sequence from smaller dilators 110 to larger dilators 110. In an embodiment, the attachment structure 112 may be a clamp that may be attached to the dilators 110 and may include the articulation joint 120 or other hinge structure. The attachment structure 112 can clamp down on the groove 106 or other portion of the needle 102.

Depending on the procedure performed and/or the size of the entry point (such as a skin entry point) created on a patient, any number of dilators 110 may be attached sequentially to the groove 106 of the needle 102. The final dilator 116, which may be one of the dilators 110, may also be attached to the groove 106 of the needle 102 and may include an opening 118 at a distal end of the final dilator 116. This opening 118 may allow the insertion of instrumentation for various operations, such as creating a fusion bed. The opening 118 may also provide a structure for bone grafting material to be delivered to a bone or a void proximate to the bone of a patient. In an embodiment, the final dilator 116 is the only dilator 110 through which bone grafting material may be pushed through. The attachment structure 112 may also include the articulation joint 120. The articulation joint 120 may enable may enable the final dilator 116 to swivel with a range of motion of at least two degrees of freedom. The ability to swivel, pivot, translate with respect to multiple axes, or rotate with such a range may allow the final dilator 116 to deposit the bone grafting material in a variety of directions relative to the needle 102 while the needle 102 is anchored in the bone of a patient. For example, while being anchored to a bone, the bone grafting material delivery device 100 may deposit the bone grafting material from one transverse process to another transverse process, from a first facet to a second facet, spinous process to spinous process, or a combination thereof.

In an embodiment, the attachment structure 112 may also include a latch mechanism 122. The latch mechanism 122 may allow any of the dilators 110 or the final dilator 116 to be locked into place when fastened. Locking the dilators 110 or the final dilator 116 in place may allow a medical professional to ensure that the dilator 110 or the final dilator 116 deposits bone grafting material in a desired location on a bone or void without having to worry about the dilators moving because of the articulation joint 120. In another embodiment, the latch mechanism 122 may be separate from the attachment structure 112. For example, the latch mechanism 122 may be placed by a medical professional at a location on the bone grafting material delivery device 100 that allows a dilator 110 or final dilator 116 to be held in a fixed position. In one embodiment, the latch mechanism 122 may be positioned proximate to the location where the attachment structure 112, articulation joint 120, and needle 102 meet. However, the latch mechanism 122 may be positioned in any other location that will enable the latch mechanism 122 to effectively lock the bone grafting material delivery device 100.

Figure 7:
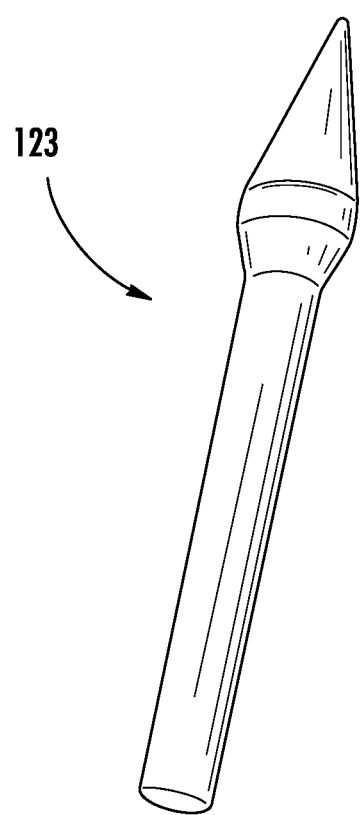
FIG. 7 is an illustration of a retractable burr that may be utilized with the bone grafting material delivery device.

In another embodiment, the bone grafting material delivery device 100 may be configured to include a retractable burr 123, as shown in FIG. 7. The retractable burr 123 may be utilized to cut, decorticate, or otherwise alter the bone of a patient so that the bone grafting material delivery device 100 can anchor effectively. In an embodiment, the retractable burr 123 may be a drill bit attached to a power source where its depth may be controlled. In another embodiment, the retractable burr 123 may not be attached to any of the components of the bone grafting material delivery device 100 and may be freestanding. The retractable burr 123 may be positioned by a medical professional through the final dilator 116 when needed. However, in yet another embodiment, the final dilator 116 may include an inner groove through which the retractable burr 123 may be attached via a side attachment of a handle of the retractable burr 123. In one embodiment, a handpiece may be utilized, by which the retractable burr 123 may retract and protrude.

Each dilator 110 and/or the final dilator 116 may include a sleeve 124 or other similar component that may be utilized to cover an opening of each dilator 110 or the opening 118 of the final dilator. In an embodiment, the sleeve 124 may be a dilator 110, as described above. The sleeve 124 may be made of metal, plastic or other suitable materials, although plastic may be preferred. The sleeve 124 may be rotated, pushed, pulled, or removed such that the sleeve 124 reveals the opening 118. In an embodiment, the sleeve 124 can rotate such that amount of the opening 118 that is expanded or revealed by the sleeve 124 is at least 50% of the circumference of the particular dilator 110 or final dilator 116 that it is covering. Additionally, the sleeve 124 may be utilized to decrease the size of the opening 118 so as to ensure that less bone grafting material is delivered at a time.

Figure 8:
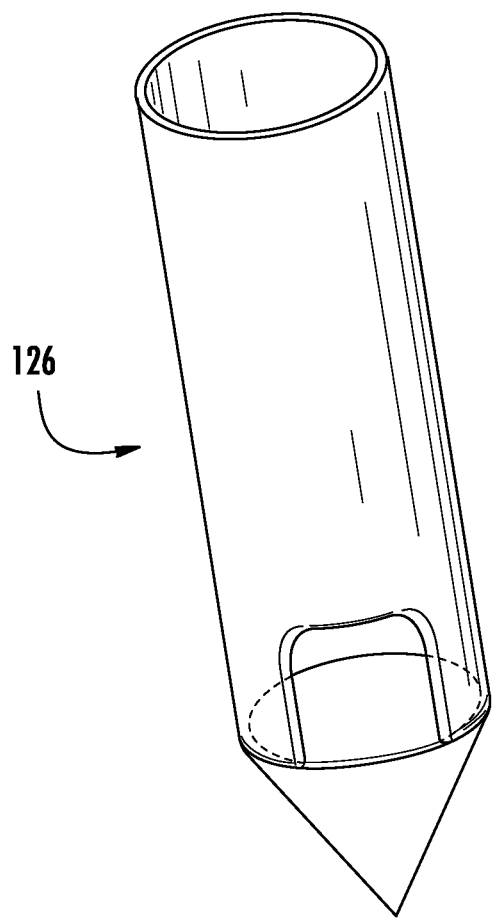
FIG. 8 is a schematic illustration depicting a trocar that may be positioned in the final dilator of the bone grafting material delivery device.
Figure 9:
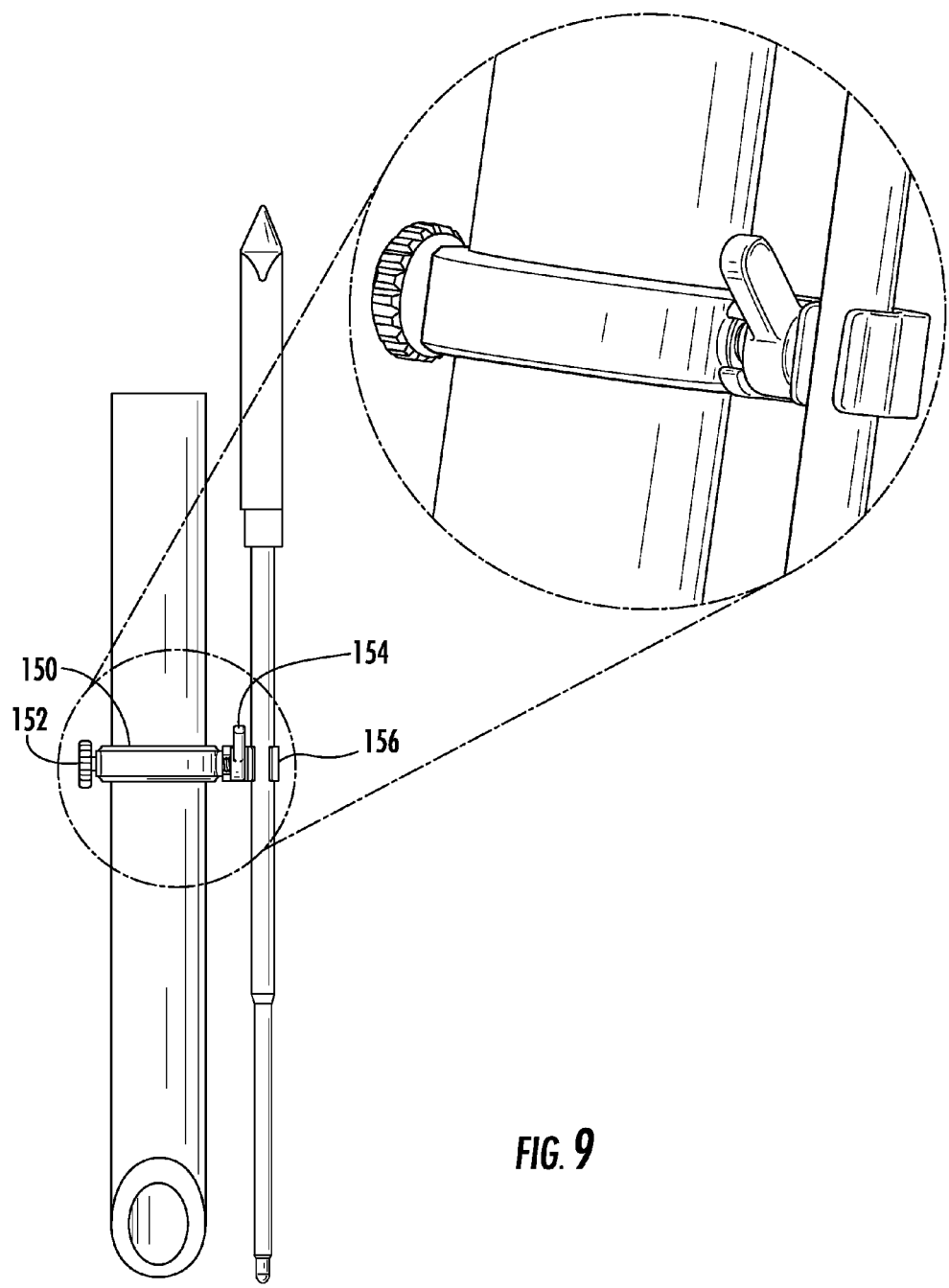
FIG. 9 is an illustration of a bone grafting material delivery device including a swivel assembly according to another embodiment.

In an embodiment, the bone grafting material delivery device 100 may also be configured to include a trocar 126, such as shown in FIG. 8. Specifically, the trocar 126 may be positioned within the final dilator 116 and may be utilized to minimize the amount of tissue that may enter the final dilator 116. For example, when the final dilator 116 is attached and is being used to deposit bone grafting material, the trocar 126 may prevent tissue from enter the opening 118 of the final dilator 116 and may prevent tissue from creeping onto the bone grafting material delivery device 100. In an embodiment, the trocar 126 may be attached to the most external part of the final dilator 116 via a slight external lip or prominence of the trocar 126. In another embodiment, there may be no static connection between the trocar 126 and the final dilator 116. In such an embodiment, the trocar 126 may be held in place during insertion. After being utilized, the trocar 126 may be removed and additional work may be conducted via the final dilator 116, such as depositing bone grafting material.

A deliver device, such as syringe 140 of the bone grafting material delivery device 100 as shown in FIG. 1, may be utilized to push the bone grafting material through the final dilator 116 and out through the opening 118 of the final dilator 116 onto a bone or into a void proximate to the bone. In an embodiment, the syringe 140 may be pressurized and may be utilized to flush material through the tube of the final dilator 116. Additionally, the syringe 140 may be freestanding, and may or may not be used multiple times.

The bone grafting material delivery device 100 may also be provided as a kit to various users. The kit may separately include the needle 102, the dilators 110, the final dilator 116, the attachment structure 112, the removable handle 108, the latch mechanism 122, the sleeve 124, the retractable burr 123, the trocar 126, the syringe 140, or various combinations of the such components. In an embodiment, the kit may be provided with the dilators 110 or the final dilator 116 already attached to the groove 106 of the needle 102 via the attachment structure 112. In another embodiment, each of the items that are part of the bone grafting delivery device 100 may be packaged separately. The kit may also include instructions for assembling and disassembling the bone grafting material delivery device 100 as well. Additionally, the instructions may include various steps for using the bone grafting material delivery device based on the type of procedure to be performed on a particular patient.

In operation, a surgeon or other qualified individual may create an entry point on a patient and position the needle 102 of the bone grafting material delivery device 100 in a selected bone of the patient. For example, as illustrated in FIG. 1, the needle 102 may be positioned into vertebral disc 130. If necessary the retractable burr 123 may be utilized to decorticate the bone prior to positioning the needle 102 into a portion of the vertebral disc 130. Additionally, a chisel or other similar devices may also be utilized as well. One location for anchoring the needle 102 may be at the pedicle 132, however, other locations are also contemplated as well. Anchoring or docking the needle 102 of the bone grafting material delivery device 100 at the pedicle 132 may be advantageous for accessing a fusion site of the spine of the patient. In order to effectively anchor the needle 102 into the vertebral disc 130, one or more dilators may be attached to the groove 106 of the needles 102 in order to dilate the bone grafting material deposit site. This may enable the bone grafting material to be deposited percutaneously.

The one or more dilators 110 and/or the final dilator may be attached to the groove 106 of the needle 102 via attachment structure 112. Once the needle 102 of the bone grafting material delivery device 100 is anchored into the bone, bone grafting material may be deposited via the opening 118 of the final dilator 116. The bone grafting material may include, but is not limited to including, at least one of an autograph, recycled bone, calcium phosphate, a synthetic, a biologic, or a combination thereof. The plunger or syringe 140, such as shown in FIG. 1, may be utilized to push the bone grafting material through the final dilator 116 and out through the opening 118. In an embodiment, the syringe 140 may be pressurized.

The bone grafting material may be deposited directionally by utilizing the articulation joint 120 of the bone grafting material delivery device 100. As noted above, the articulation joint 120 may enable the dilators 110 and/or the final dilator 116 to articulate or swivel in multiple degrees of freedom so as to allow the bone grafting material to be deposited in various locations. For example, the bone grafting material delivery device 100 may be configured to deposit bone grafting material percutaneously from one transverse process 134 to another transverse process 134, from a spinous process 138 to another spinous process 138, from a facet 136 to another facet 136, from any part of the vertebral disc 130 to a void or process, or any combination thereof. As the bone grafting material is being deposited by the bone grafting material delivery device 100, a bone graft scaffold including the bone grafting material can be created between specific points so as to allow desired portions of bone to fuse together over time, such as during spinal fusion surgery. The deposited bone grafting material may stimulate the desired portions of bone to grow in a desired direction and manner.

As the bone grafting material is being applied, the trocar 126 may be inserted into the final dilator 116 so as to minimize the amount of tissue that creeps into the opening 118 of the final dilator 116 or into any other part of the bone grafting material delivery device 100. Additionally, in order to regulate the quantity of bone grafting material that is delivered to the fusion site, the sleeve 124 of the final dilator 116 may be rotated or adjusted to increase or decrease the size of the opening 118 of the final dilator 116 accordingly. Also, if a particular amount of bone grafting material is intended to be deposited at a specific location, the latch mechanism 122 may be utilized to lock the dilators 110 or the final dilator 116 into place. When bone grafting material needs to be applied at other locations, the latch mechanism 122 may be unlocked or otherwise removed to allow the articulation joint 120 to move freely. Once the procedure is finished, the medical professional may then safely remove the bone grafting material delivery device 100 from the body of the patient.

Referring to the drawings and in particular to FIGS. 7-15B, a bone grafting material delivery device 200 is schematically illustrated. The bone grafting material delivery device 200 may include a needle 140, one or more dilators 141, and a final dilator 142. Notably, the one or more dilators 141 and the final dilator 142 may be attached in sequence to the needle 140 via a swivel assembly 145. The dilators 141 and the final dilator 142 can be configured to articulate in a variety of directions with respect to the needle 140 by using the swivel assembly 145. The bone grafting material delivery device 200 may also include a syringe 140 as described herein, through which the bone grafting material may be pushed through the final dilator 142 onto a bone or in a void proximate to the bone of the patient.

The needle 140 of the bone grafting material delivery device 200 may be a Jamshidi needle or other suitable needle. The needle 140 may include a cutting edge 104 that may be utilized to cut into a bone of an individual and, as a result, enable the needle 102 to anchor into the patient's bone. Unlike needle 102, the needle 140 may not include a groove for attaching to the dilators 141 and final dilator 141. Instead, the needle 140 may have a smooth surface in place of the groove that is found on needle 102. The needle 140 may include markers of an appropriate distance (e.g. 10 cm) that are positioned along various portions of the needle 140.

The needle 140 may include a detachable or removable handle 108 that may be located at a proximal end of the needle 140. The removable handle 108 may screw into the proximal end, snap into the proximal end, or otherwise fasten or connect to the proximal end of the needle 140. Additionally, the removable handle 108 may include grooves to allow an individual to grip the removable handle 108. The removable handle 108 may allow a physician or other medical professional to easily hold the needle 140.

The one or more dilators 141 of the bone grafting material delivery device 100 may be similar to dilators 110 and may be utilized to dilate a surgical area of a patient and to deliver the bone grafting material to a bone and/or in a void area of a patient. The dilators 141 may be made of similar materials as used for dilators 110 and may also have varying lengths, heights, widths, and circumferences. The dilators 141 may come in various shapes and may be for single or multiple use. However, instead of using attachment structure 112 to connect to the needle 140, each dilator 141 and/or the final dilator 142 may be connected to the needle 140 by utilizing a swivel assembly 145, described below.

The swivel assembly 145 of the bone grafting material delivery device 200 may include a dilator ring 150, a knob assembly 152, a stud 153, a lock lever 154, and a clamp assembly 156. The swivel assembly 145 may be utilized to attach the needle 140 to the dilators 141 or 142. Once the needle 140 and the dilators 141 or 142 are attached to the swivel assembly 145, a physician may use the swivel assembly 145 to rotate the dilators 141 or 142 in various directions with respect to the needle 140. The dilators 141 or 142 may be angled towards or away from the needle 140. As a non-limiting example, the dilators 141 or 142 can have a medial to lateral range of motion of at least 8 degrees. For instance, a physician may angle the dilators 141 or 142 towards an insertion point near the deposit site. As a result, the bone graft material may be deposited in various different locations with precision as the needle 140 is docked onto a patient's bone. In one embodiment, the swivel assembly 145 may allow the needle 140 to rotate about its longitudinal axis so that a physician may spin the needle 140 in place as needed. In another embodiment, the dilators 141 or 142 may be configured to rotate around the needle 140 using the swivel assembly 145 or vice versa.

The dilator ring 150 of the swivel assembly 145 may be generally annular with an inner circumference that may be slightly larger than the outer circumference of the dilator 141 or 142, such that the dilator ring 150 can be slid over the dilator 141 or 142. The dilator ring can have at least two bores 157 and 158 that extend transversely through the wall of the dilator ring 150. The wall of the dilator ring 150 adjacent to the first bore 157 can be thicker than the wall of the majority of the dilator ring 150 such that a protruding ridge 148 is formed around the first bore 157 along the exterior of the dilator ring 150. The protruding ridge 148 can extend the entire height of the wall of the dilator ring 150. The protruding ridge 148 can have a substantially flat outer surface while the inner circumference of the dilator ring 150 maintains its generally annular curvature.

The first bore 157 extending transversely through the wall of the dilator ring 150 can be sized to receive knob assembly 152, which may include knob handle 166 and knob shaft 168. First bore 157 can be internally threaded to accept the threaded knob shaft 168, which can have enough length to pass through the first bore 157 and contact the dilator 141 or 142 when rotated to a tightened position. In such an arrangement, the knob assembly 152 can be used as tensioning screw to detachably secure the dilator ring 150 to a specific point along the length of the dilator 141 or 142.

The dilator ring 150 can have a second bore 158 extending transversely through the wall of the dilator ring 150, and the first bore 157 and second bore 158 can be on opposite sides of the dilator ring 150 such that the longitudinal axis of the respective bores lie along a diameter of the dilator ring 150. The second bore 158 can be sized to accept stud 153, which can include stud shaft 170 and stud head 171, and can have internal threading to match the threading of stud 153.

The internal surface of the dilator ring 150 adjacent to the second bore 158 can have a recessed concave surface 149. The stud head 171 can have a convex surface that corresponds to the concavity of the recessed concave surface 149. The recessed concave surface 149 reaches a depth within the wall of the dilator ring 150 such that when the stud 153 is inserted in the second bore 158, the stud head 171 of stud 153 lays within the recessed concavity, either level with or recessed from the interior surface of the dilator ring 150 to ensure a smooth contact surface between the dilator 141 or 142 and the interior surface of the dilator ring 150. In this arrangement, the stud head 171 and the interior surface of the dilator ring 150 can combine to form a continuous surface of generally a constant curvature.

At the exterior of the dilator ring 150 adjacent to the second bore 158 can include an articulation surface 159. The articulation surface 159 of the dilator ring 150 may be formed by a ridged surface that protrudes beyond the width of the majority of the dilator ring 150 to form a generally flat plateau 147. The approximate center of the generally flat plateau 147 can include a protruding convex surface 147 of a generally circular shape. The curvature of the protruding convex surface 147 can generally match the curvature of the dilator ring 150 or have a different curvature. Additionally, the protruding convex surface 147 can include a recessed generally concave surface 146 at the approximate apex of the protruding convex surface 147, which is generally within the approximate center of the protruding convex surface 147.

Figure 10A:
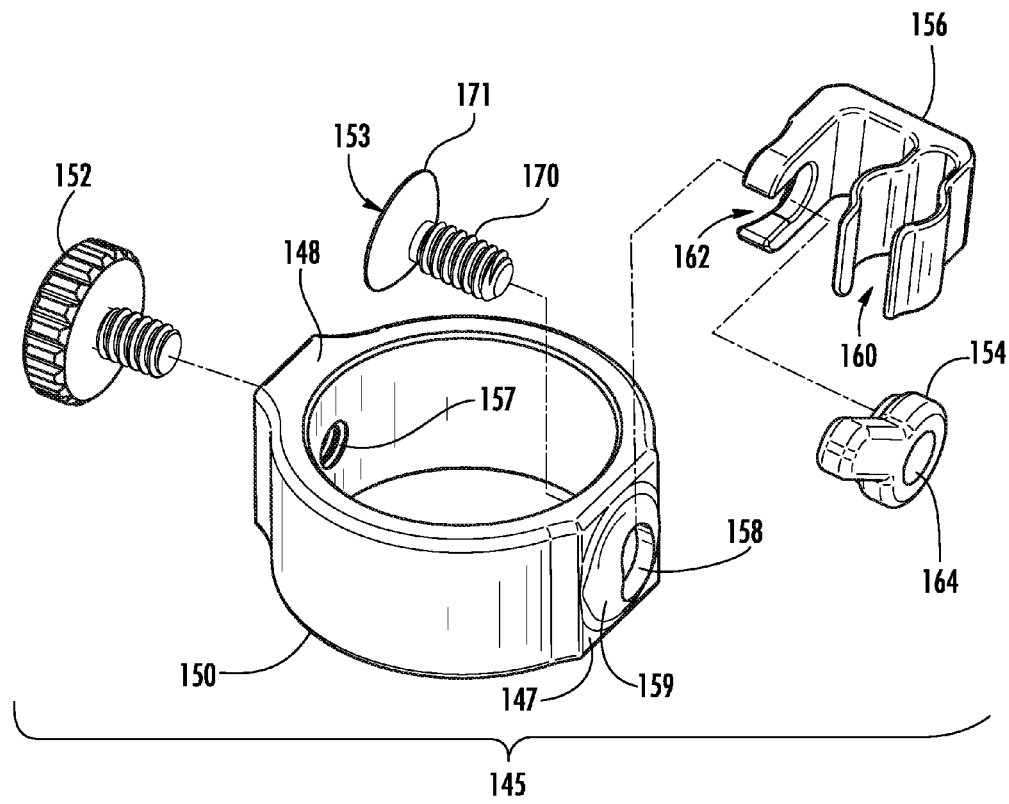
FIG. 10A is an illustration depicting an exploded view of the swivel assembly from FIG. 9.

The dilator ring 150 may be further secured to the dilator 141 or 142 by screwing in the stud 153 through the second bore 158 as shown in FIG. 10A. When the stud 153 is inserted into the second bore 158 of the dilator ring 150, the stud shaft 170 protrudes beyond the articulation surface 159, including beyond the width to which the protruding convex surface 147 extends. As described below, the protruding convex surface 147 and the recessed surface 146 of the articulation surface 159 form an articulating joint with indented portion 161 of the clamp assembly 156.

The clamp assembly 156 shown in FIG. 10A can include a joint portion 173 and a clamping portion 160. The joint portion 173 can include two arms 174a and 174b that provide an opening 162 through which stud 170 can be accepted or inserted. The exterior of two arms 174a and 174b combine to form an indented surface 161, that may be a generally concave surface. The concavity of the indented surface 161 may correspond to the concavity of the protruding convex surface 147 of the articulation surface 159 on the dilator ring 150. The protruding convex surface 147 of the articulation surface 159 and the indented portion 161 of the clamp assembly 156 may have anatomically matching surfaces, such as concave, convex, or have any other shapes, which allows the creation of the articulating joint. The corresponding generally partially spherical convex and concave surfaces allow for multiple degrees of freedom when the corresponding surfaces articulate against each other. As non-limiting examples, the corresponding surfaces can translate in three axial directions with respect to each other and they can also rotate with respect to each other.

The clamp assembly 156 can also include a second opening 175 between the clamp portion 160 and the joint portion 173. The second opening can be sized to receive the lock lever 154 or other locking device for securing the claim 156 to the dilator assembly 150. The lock lever 154 may include a head 176 with a bore 164 into which the stud 170 can be screwed or otherwise fastened. The bore 164 can be threaded or unthreaded, and can extend through the head 176 or only partially into head 176. The opposite end of the lock lever 154 from the bore 164 is the tip 177 that can be moved by a user to lock or release the lock lever 154.

The clamp portion 160 can include two opposing arms 178a and 178b that form a clamp. Each opposing arm 178a and 178b includes a generally centrally located concave internal surface 179a and 179b designed to match the curvature of the outer surface of needle 140. The distance between the two opposing arms 178a and 179b can vary depending on the size of the needle 140 to which the clamp assembly 156 will be secured. The two opposing arms 178a and 179b can also be made of a material that will slightly flex outward when wrapped around a need 140 so that the two opposing arms 178a and 179b attached securely, but removably to the needle 140. The arms 178a and 179b can also include outward bent tips. The two opposing arms 178a and 179b may also allow the needle 140 to rotate about its longitudinal axis such that the needle 140 may be spun in a circular fashion while generally retained within the clamp assembly 156.

Figure 10B:
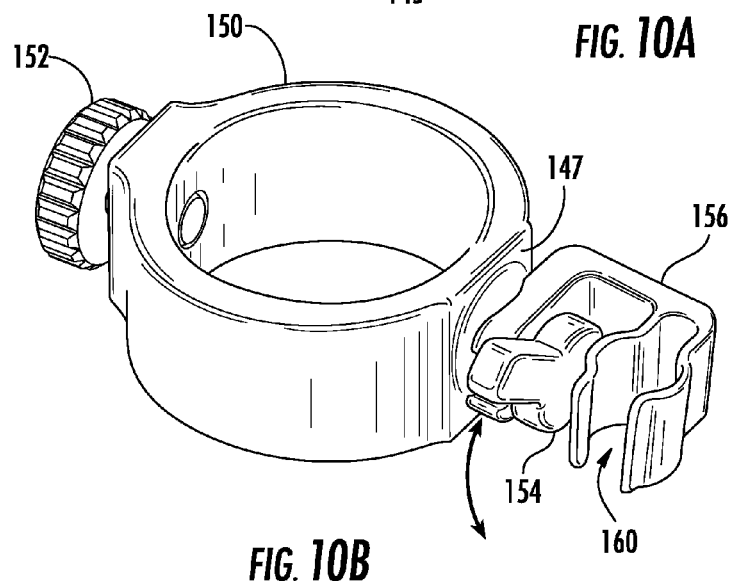
FIG. 10B is an illustration depicting the swivel assembly from FIG. 9.
Figure 11A:
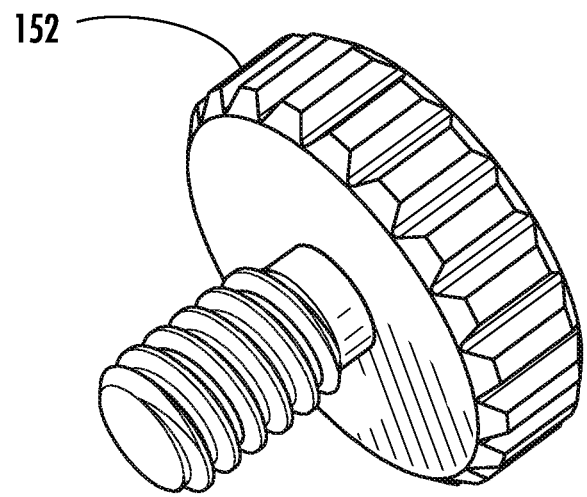
FIG. 11A is an illustration depicting a knob assembly utilized with the swivel assembly of FIG. 9.
Figure 11B:
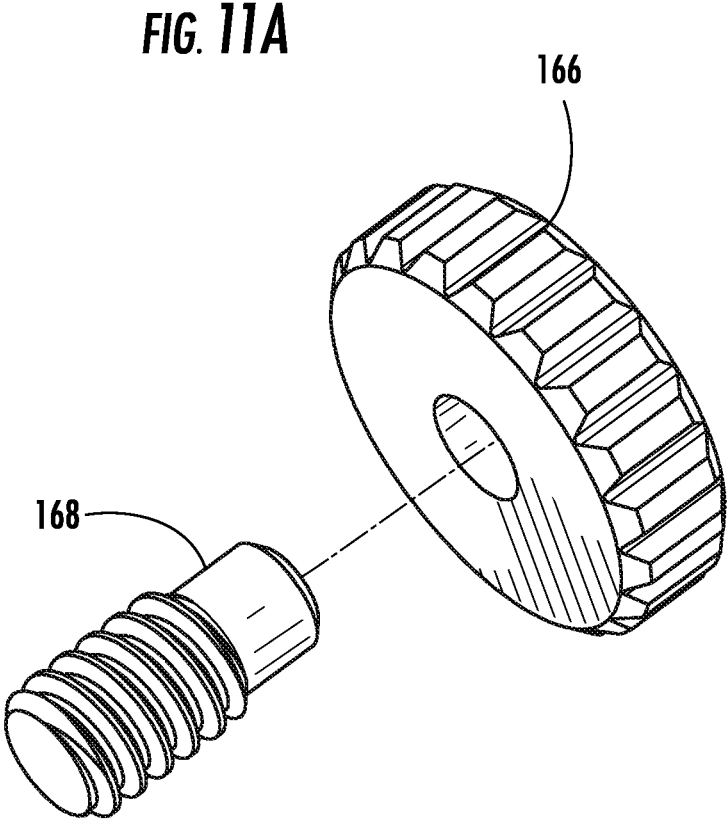
FIG. 11B is an illustration depicting an exploded view of the knob assembly utilized in the swivel assembly of FIG. 9.
Figure 12A:
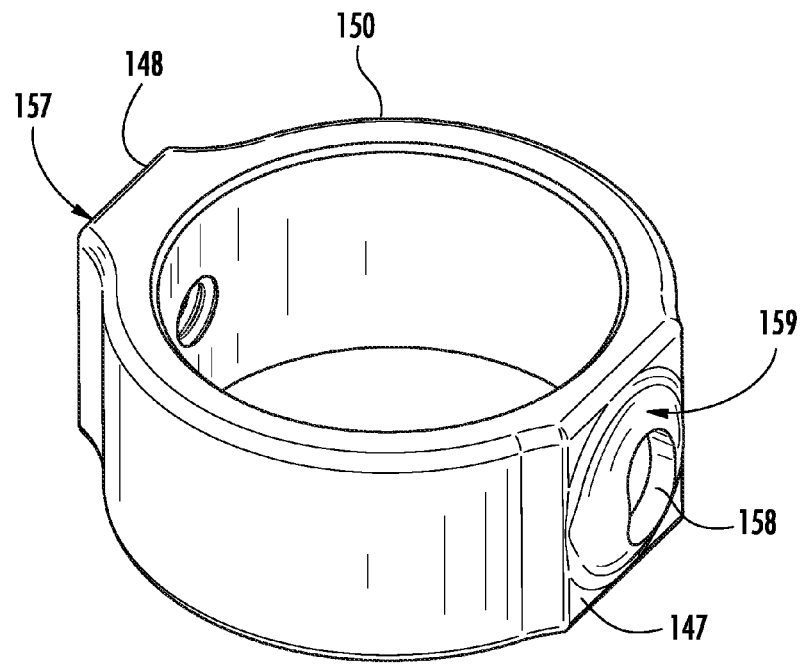
FIG. 12A is an illustration depicting a dilator ring utilized in the swivel assembly of FIG. 9.
Figure 12B:
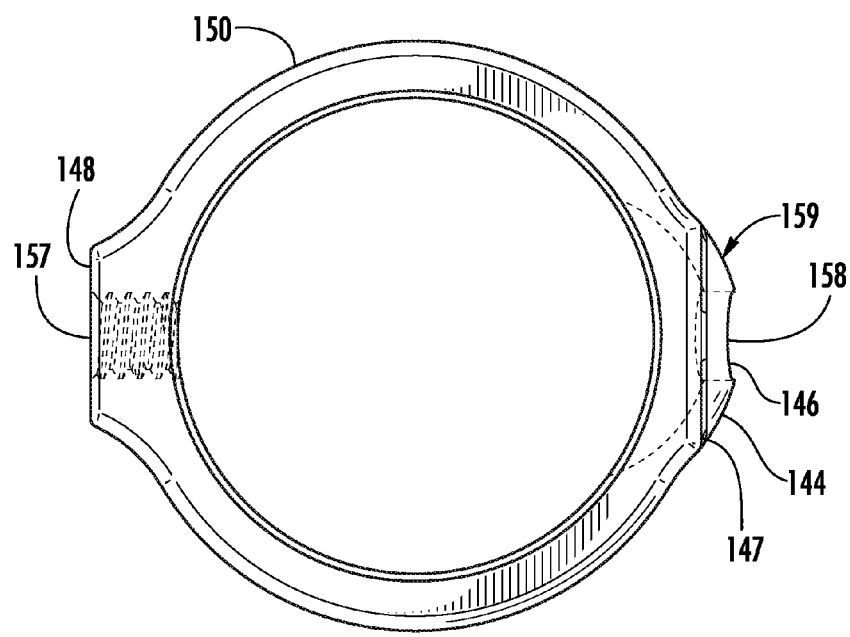
FIG. 12B is an illustration depicting a top view of the dilator ring of FIG. 12A.
Figure 13A:
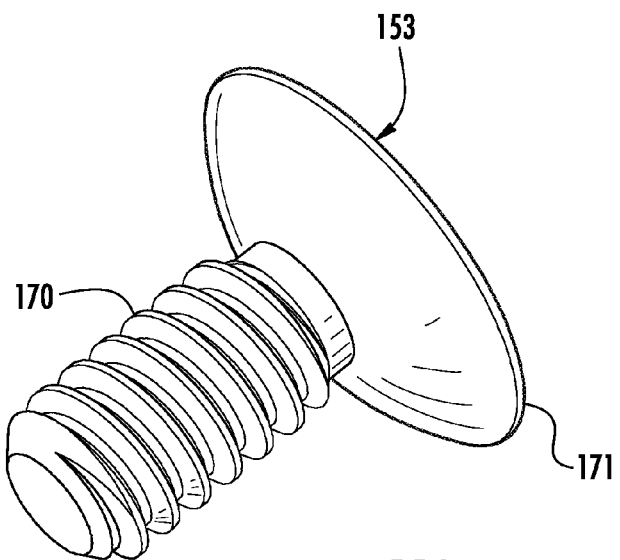
FIG. 13A is an illustration depicting a stud utilized in the swivel assembly of FIG. 9.
Figure 13B:
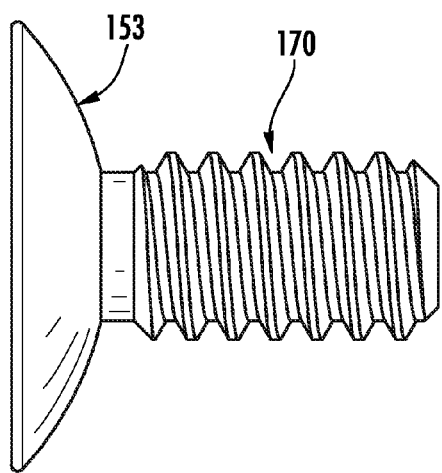
FIG. 13B is a side view of the stud of FIG. 13A.
Figure 13C:
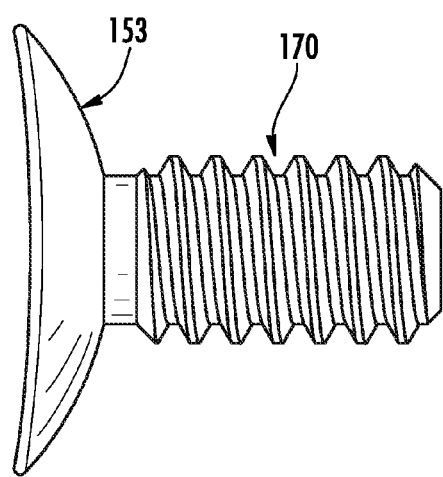
FIG. 13C is a side view of an alternative embodiment of a stud.
Figure 14A:
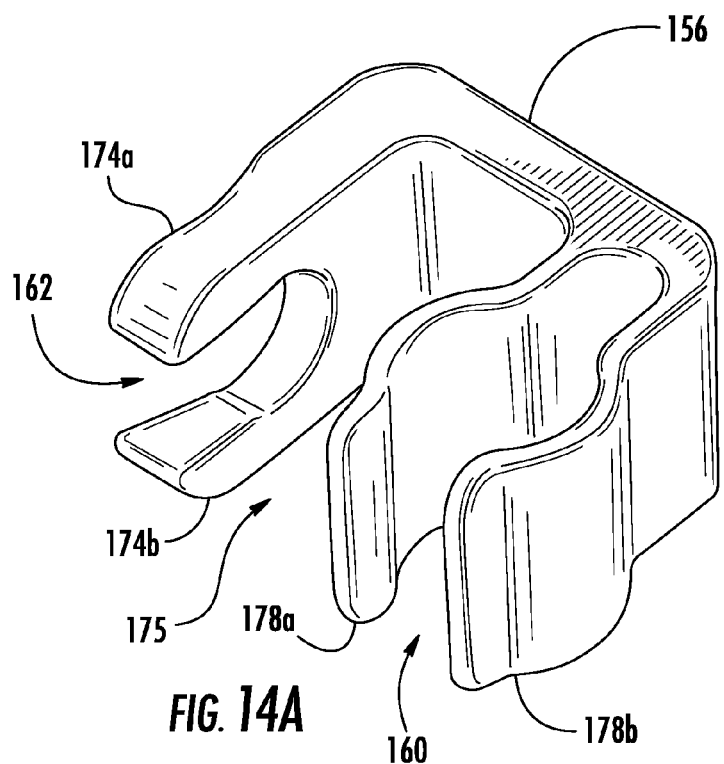
FIG. 14A is an illustration depicting a clamp utilized in the swivel assembly of FIG. 9.
Figure 14B:
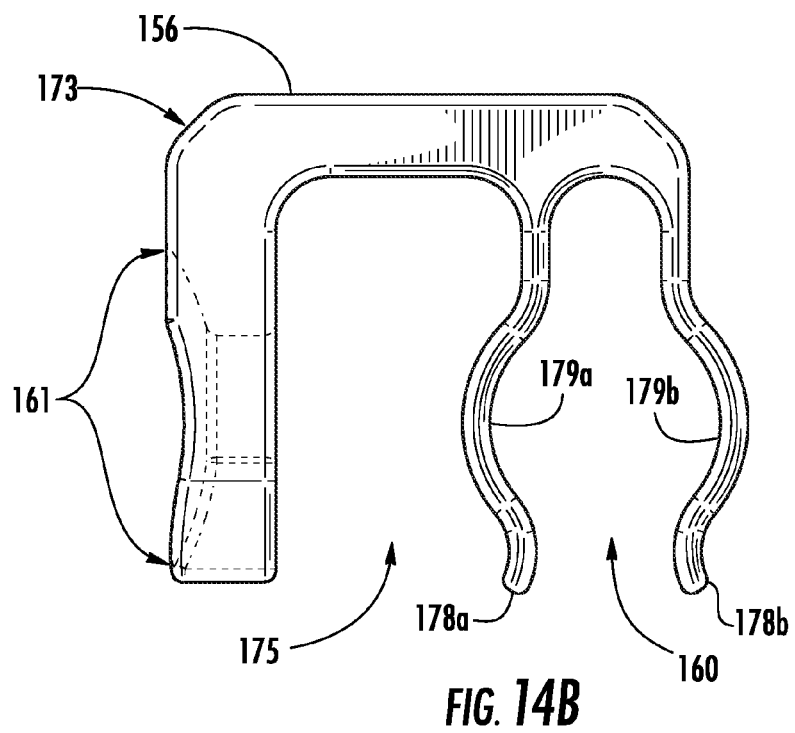
FIG. 14B is an illustration of a top view of the clamp of FIG. 14A.
Figure 15A:
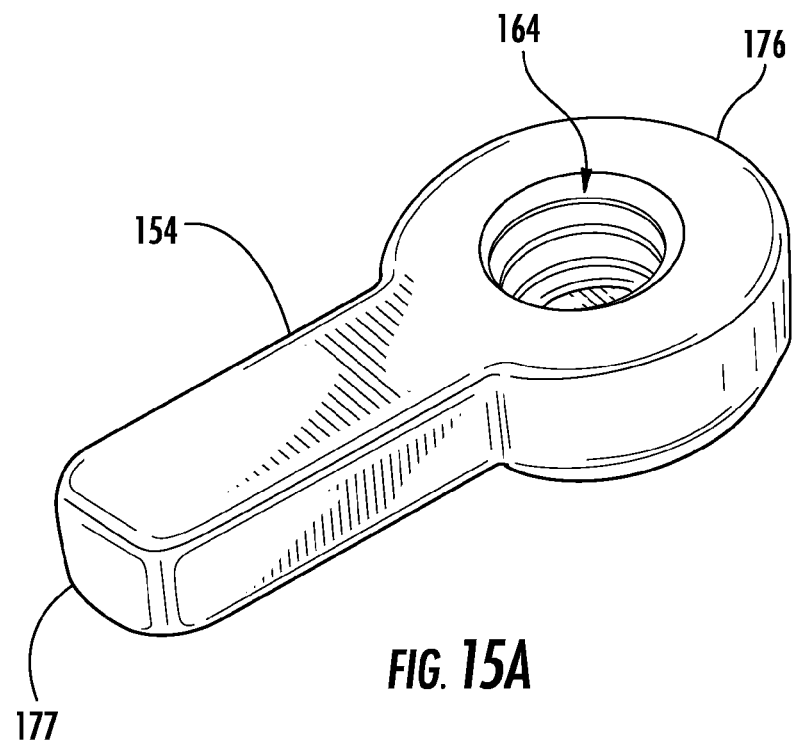
FIG. 15A is an illustration depicting a lock lever utilizing in the swivel assembly of FIG. 9.
Figure 15B:
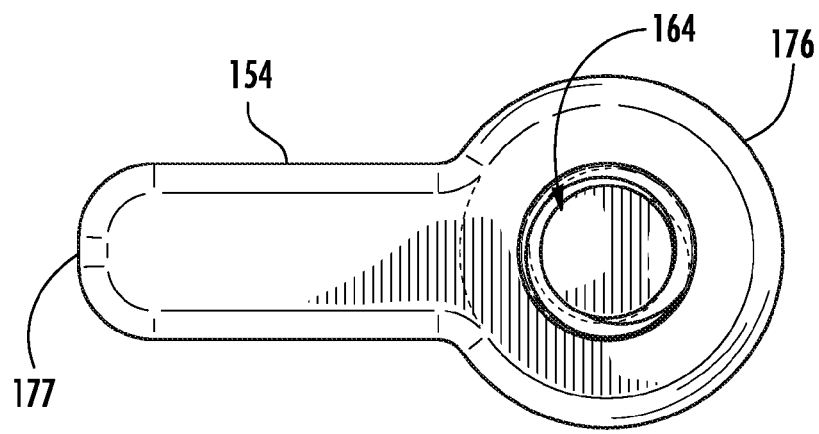
FIG. 15B is an illustration of a top view of the lock lever of 15A.

In combination with the ring dilator 150, the lock lever 154 of the clamp assembly 156 can be used to lock the dilators 141 or 142 into a desired fixed position so that the bone grafting material may be deposited effectively. In order to attach the clamp assembly 156 to the swivel assembly 145 as shown in FIGS. 10A and 10B, the stud 173 can be inserted through the second bore 158, through opening 162 of the clamp assembly 156 and into lock lever 154. In this arrangement, the opening 162 may be positioned over a portion of the shaft 170 of the stud 153 that juts out of the dilator ring 150 that is between the lock lever 154 and the second bore 158 of the dilator ring 150. When the opening 162 is positioned on the portion of the shaft 170 such that the indented surface 161 creates an articulating joint with the articulation surface 159, the lock lever 154 can rotate the shaft 170 when the lock lever 154 is pivoted. In another arrangement, instead of rotating the shaft 170, the lock lever 154 can pivoted, such that the threading of the shaft 170 cooperates with the threading 164 of the lock lever 154, to move the lock lever 154 relative to the shaft 170 and in the direction of the dilator 150 to secure the swivel assembly 145 in a fixed arrangement or moved relative to the shaft 170 in the direction away from the swivel assembly 145 to an unfixed arrangement. In this regard, the lock lever 154 can be moved to a locked position to secure the components or an unlocked position to allow free movement by decreasing and increasing the distance between ring dilator 150 and the clamp assembly 156. In order to adjust the position of a dilator 141 or 142 secured to the dilator ring 150, the lever can be pivoted to an unlocked position, which will allow the dilator 141 or 142 to articulated with respect to the claim assembly 156. The position of the dilator 141 or 142 can be secured again by moving the lock lever 154 to the locked position.

If the physician holds the clamp assembly 156 in place, the physician may rotate the dilators 141 and/or the final dilator 142 in various directions when the lock lever 154 is in an unlocked position. When the lock lever 154 is in a locked position, the clamp assembly 156 may be held in place relative to the dilator 150. The needle 140 may be attached to the clamp assembly 156 by inserting a portion of the needle 140 into the clamp portion 160. Once inserted into the clamp portion 160, the needle 140 may be securely attached to the bone grafting material delivery device 200.

In another embodiment, the bone grafting material delivery device 200 may be configured to include the retractable burr 123, the sleeve 124 for covering an opening of each dilator 141 or the opening of the final dilator 142, and the trocar 126.

The bone grafting material delivery device 200 may also be provided as a kit. The kit may separately include the needle 140, the dilators 141 the final dilator 142, the swivel assembly 145, the removable handle 108, the sleeve 124, the retractable burr 123, the trocar 126, the syringe 140, or various combinations of such components. In an embodiment, the kit may be provided with the dilators 141 or the final dilator 142 already attached to the swivel assembly 145 using dilator ring, 150, knob assembly 152, and stud 153. In another embodiment, each of the items that are part of the bone grafting delivery device 200 may be packaged separately. The kit may also include instructions for assembling and disassembling the bone grafting material delivery device 200 as well. Additionally, the instructions may include various steps for using the bone grafting material delivery device 200.

In operation, a physician or other individual may utilize the bone grafting material delivery device 200 to deliver bone grafting material to a selected site of a patient. The physician may create an entry point at or near the surgical site and position needle 140 into the clamp portion 160 to securely attach the needle 140 to the swivel assembly 145. The physician may then proceed to position the needle 140 into the desired bone. Once the needle 140 is appropriately positioned, the needle 140 may serve as a dock for allowing the physician to readily access a fusion site of the patient. Once the needle 140 is docked into the bone, the dilators 141 and/or the final dilator 142 may be attached to the swivel assembly 145 by positioning the dilator ring 150 at a selected location on the body of dilators 141 and/or final dilator 142 and attaching them to the dilator ring 150 using the knob assembly 152 and/or stud 153. After the dilators 141 and/or the final dilator are attached to the bone grafting material delivery device 200, the physician may dilate the skin and tissue of the bone grafting material deposit site such that the bone grafting material may be deposited percutaneously via an opening of the final dilator 142. The plunger or syringe 140 may be utilized to push the bone grafting material onto the deposit site via the final dilator 142. In one embodiment, the dilators 141 and/or the final dilator 142 may be positioned at or near the surgical site first and then the needle 140 may be inserted into the clamp assembly 156.

Once the physician is finished depositing the bone grafting material at a particular deposit site, the swivel assembly 145 may be utilized by the physician to adjust the position of the dilators 141 and/or the final dilator 142 with respect to the needle 140 so that the dilators 141 and/or the final dilator 142 may access another fusion site. In order to do so, the physician may partially unscrew the lock lever 154 so that the dilators may swivel in a desired direction. After the dilator 141 and/or the final dilator 142 is positioned into the desired direction, the physician may refasten the lock lever 154 so that the dilators may be locked in place for depositing the bone grating material again. The physician may keep repeating this procedure until the operation is completed and as long as necessary. In an embodiment, the physician may deposit the bone grafting material at the deposit site while swiveling the dilator 141 and/or the final dilator 142 in desired directions. Once the operation is completed, the physician may remove the bone grafting material delivery device 200 from the patient's surgical site.

The swivel assembly 145 is not limited to use in connection with needles and/or dilators for delivering biologics or preparing fusion sites. The swivel assembly 145 can be detachably coupled to a variety of instruments to provide a fixed structure one side and an operating device or tube that can articulate in at least two degrees of freedom. The swivel assembly can be coupled to a first anchoring structure, such as any generally cylindrical object, with a clip assembly 156 where the anchoring structure is docked to a particular site on a patient. The other end of the swivel assembly 145, such as annular ring 150, can be detachably coupled to any generally cylindrical tube or instrument. As a non-limiting example, the cylindrical tube may provide a pathway for optical instrumentation to view a deep tissue or bony area.

Figure 16:
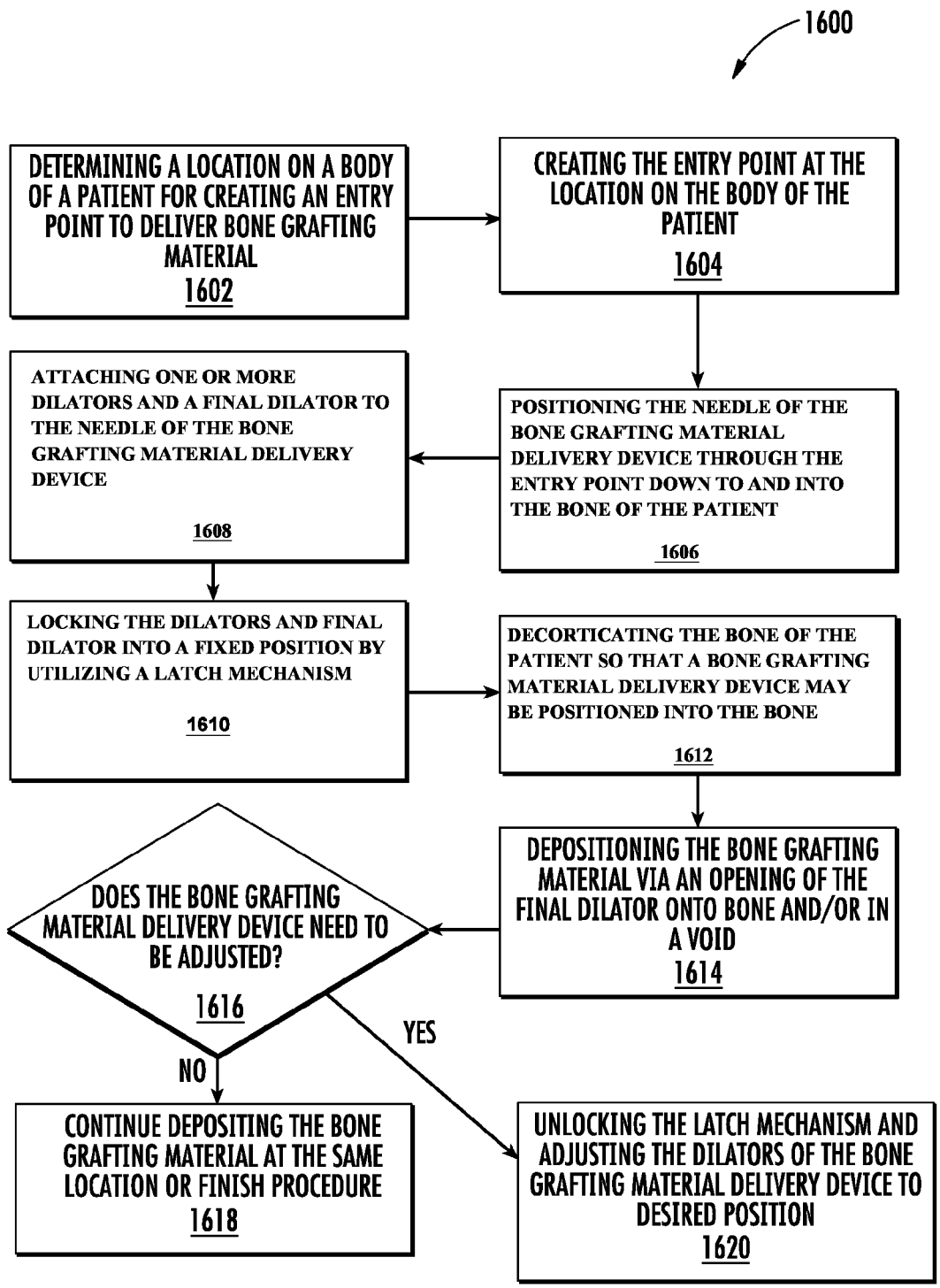
FIG. 16 features a method for delivering bone grafting material according to an exemplary embodiment.

Referring now also to FIG. 16, an exemplary method 1600 for delivering bone grafting material is schematically illustrated. The method 1600 may include, at step 1602, determining a location on a body of a patient for creating an entry point to deliver bone grafting material. For example, the location may be a part of the spine of the patient or any other suitable location. At step 1604, the method 1600 may include creating the entry point at the location on the body of the patient. The method 1600 may include positioning the needle 102 into a part of the bone for which bone grafting material needs to be deposited at step 1606. Once, the needle 102 is effectively positioned it may act as an anchor for the bone grafting material delivery device 100. Notably, in an embodiment, the retractable burr 123 may be connected to the bone grafting material delivery device 100 and the bone may be decorticated after positioning the bone grafting material delivery device 100 into the bone.

At step 1608, the method 1600 may include attaching one or more dilators 110 and a final dilator 116 to a portion of the needle 102. For example, the dilators 110 and the final dilator 116 may be attached to the groove 106 of the needle 102 via the attachment structure 112. The dilators 110 and/or the final dilator 116 may be attached sequentially or in a variety of other manners to the groove 106. Additionally, the dilators 110 and the final dilator 116 may articulate in a variety of directions via an articulation joint 120. The method 1600 may include, at step 1610, locking the dilators 110 and/or the final dilator 116 into a fixed position with respect to the needle 102 by utilizing the latch mechanism 122. The method 1600, at step 1612, may also include decorticating or otherwise altering a bone of the patient so that the bone grafting material delivery device 100 may be effectively positioned into the bone. The bone may be decorticated by using the retractable burr 123. Once the bone is decorticated appropriately, the burr 123 may be retracted by the medical professional performing the procedure.

At step 1614, the method 1600 may include depositing the bone grafting material via the opening 118 of the final dilator 116 onto the bone of the patient and/or into a void proximate to the bone of the patient. The bone grafting material may be deposited by utilizing a pressurized syringe 140 to push the bone grafting material through the opening 118 of the final dilator 116. At step 1616, the method 1600 may include determining if the bone grafting material delivery device 100 needs to be adjusted. If the bone grafting material delivery device 100 does not need to be adjusted, the method 1600 may include continuing to deposit the bone grafting material at the same location or finishing the procedure at step 1618.

If, however, the bone grafting material delivery device 100 needs to be adjusted, the method 1600 may include, at step 1620, unlocking or otherwise removing the latch mechanism 122 so that the dilators 110 and/or the final dilator 116 may be adjusted via the articulation joint 120 to a desired position. This may be performed so that the bone grafting material may be deposited in other locations without having to remove the needle 102 from the bone of the patient. Once, the dilators 110 and/or the final dilator 116 is move to the desired position, the method 1600 may include relocking them into position so that the bone grafting material may be deposited. In an embodiment, the method 1600 may include positioning a trocar 126 into the final dilator 116 and then utilizing the trocar 126 to minimize the amount of tissue that enters the opening 118 of the final dilator or that surrounds the bone grafting material delivery device. In another embodiment, the method 1600 may include adjusting the size of the opening 118 of the final dilator 116 so as to regulate the amount of bone grafting material that is deposited at a given time. The size of the opening 118 may be increased or decreased by utilizing a structure such as sleeve 124.

Figure 17:
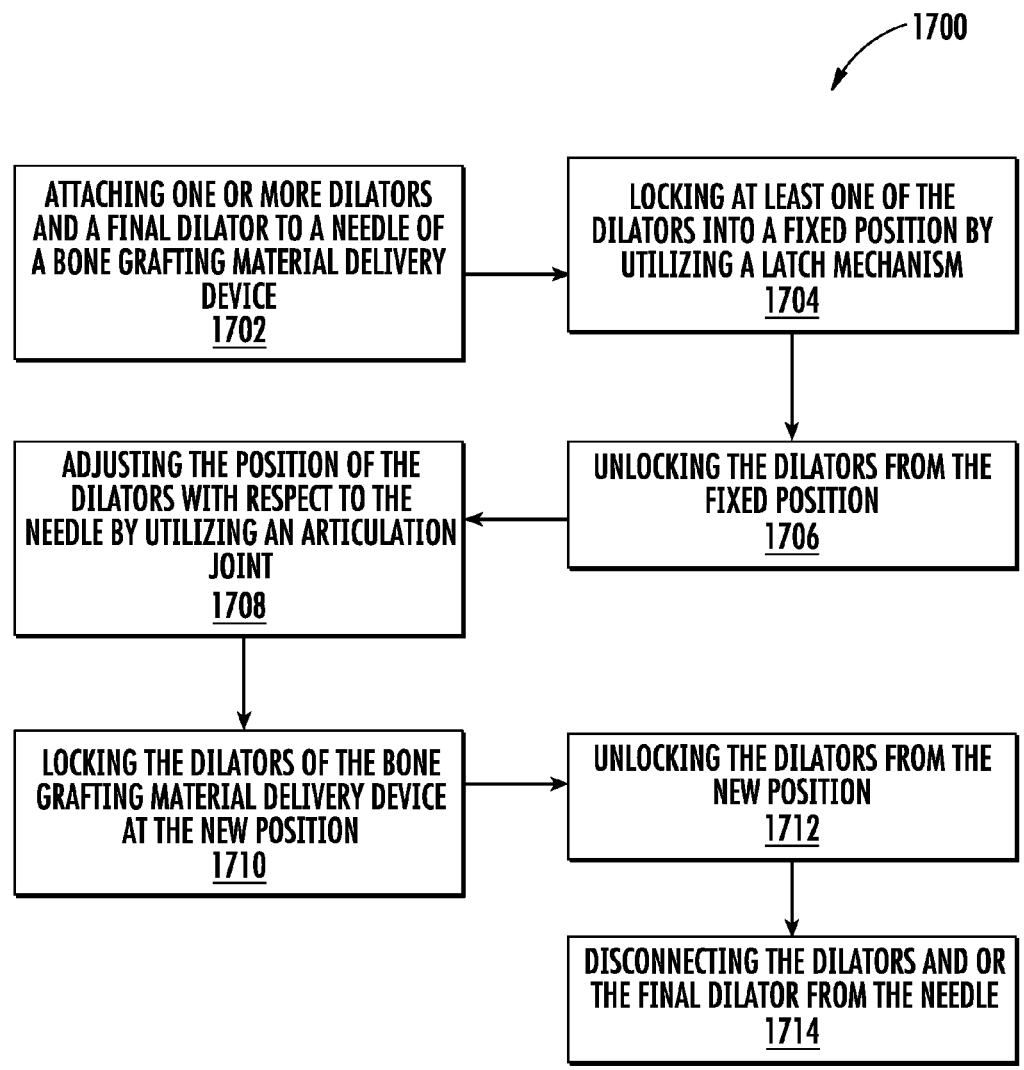
FIG. 17 features a method for assembling and disassembling a bone grafting material delivery device according to an exemplary embodiment.

Accordingly to an embodiment as illustrated in FIG. 17, a method 1700 for assembling and disassembling a bone grafting material delivery device may also be provided. The method 1700, at step 1702, may include attaching one or more dilators 110 and/or a final dilator 116 to a needle 102 of a bone grafting material delivery device 100. The one or more dilators 110 and/or the final dilator 116 may be attached sequentially or in a variety of other manners. The dilators 110 and/or the final dilator 116 may be attached to a groove 106 of the needle 102. At step 1704, the method 1700 may include locking the dilators 110 and/or the final dilator 116 into a fixed position by utilizing a latch mechanism 122. Additionally, the method 1700 may include unlocking the dilators 110 and/or the final dilator 116 at step 1706. Once unlocked, the method 1700 may include adjusting the position of the dilators 110 and/or the final dilator 116 with respect to the needle 102 by utilizing an articulation joint 120 of the bone grafting material delivery device 100 at step 1708. After the position is adjusted, the method 1700 may include locking the dilators 110 and/or the final dilator 116 at the new position at step

1710. Once the bone grafting material delivery device 100 is no longer needed or the procedure is completed, the method 1700 may include unlocking the dilators 110 and/or the final dilator 116 at step 1712. The method 1700 may then include disconnecting the dilators 110 and/or the final dilator 116 from the needle 102 at step 1714.

Optionally, the method 1700 may include connecting a retractable burr 123 to the bone grafting material delivery device 100 for decorticating bone. As another option, the method 1700 may include positioning the trocar 126 into the final dilator 116 of the bone grafting delivery device 100. As yet another option, the method 1700 may include positioning the syringe 140 into the final dilator 116. As still another option, the method 1700 may include removing the attachment structure 112 from the dilators 110 and/or the final dilator 116.

Figure 18:
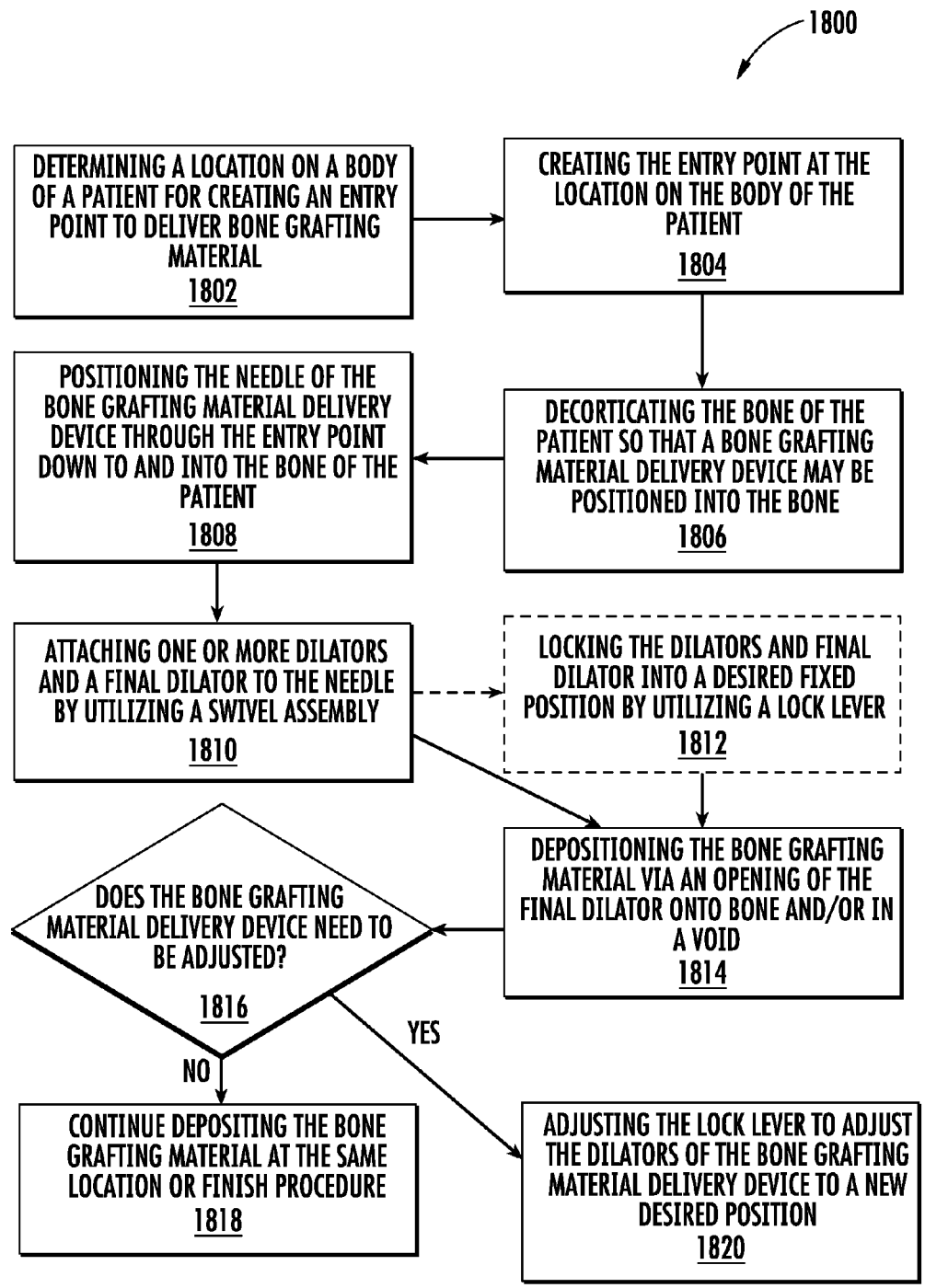
FIG. 18 features a method for delivering bone grafting material using a bone grafting delivery device having a swivel assembly according to an exemplary embodiment.

Referring now to FIG. 18, an exemplary method 1800 for delivering bone grafting material utilizing a bone grafting delivery device including a swivel assembly 145 is schematically illustrated. The method 1800 may include, at step 1802, determining a location on a body of a patient for creating an entry point to deliver bone grafting material. At step 1804, the method 1800 may include creating the entry point at the location on the body of the patient. The method 1800, at step 1806, may also include decorticating or otherwise altering a bone of the patient so that the bone grafting material delivery device 200 may be effectively positioned into the bone. Additionally, the method 1800 may include positioning the needle 140 into a part of the bone for which bone grafting material needs to be deposited at step 1808.

At step 1810, the method 1800 may include attaching one or more dilators 141 and a final dilator 142 to a portion of the needle 140 by utilizing a swivel assembly 145. The dilators 141 and/or the final dilator 142 may be sequentially attached or attached in a variety of different configurations. The dilators 141 and the final dilator 142 may be attached to the swivel assembly 145 by utilizing a dilator ring 150 that may be secured to the dilators 141 and the final dilator 142 by utilizing a knob assembly 152 and stud 153. As described herein, the dilators 141 and the final dilator 142 may articulate in a variety of directions via the swivel assembly 145. The needle 140 may be secured to the swivel assembly 145 by being clamped into a clamp assembly 156 of the swivel assembly 145. In an embodiment, the needle 140 may be spun around its longitudinal axis while secured in the swivel assembly 145. The method 1800 may include, at step 1812, optionally locking the dilators 141 and/or the final dilator 142 into a desired position by utilizing the lock lever 154. However, instead of locking the dilators 141 and the final dilator 142, the method 1800 may proceed directly to step 1814 from step 1810. At step 1814, the method 1800 may include depositing the bone grafting material via an opening of the final dilator 142 onto the bone of the patient and/or into a void proximate to the bone of the patient. If the dilators 141 and/or the final dilator 142 are not in a locked position, then the bone grafting material may be deposited while the dilators 141 and/or the final dilator 142 are being swiveled in a variety of directions. At step 1816, the method 1800 may include determining if the bone grafting material delivery device 200 needs to be adjusted. If the bone grafting material delivery device 200 does not need to be adjusted, the method 1800 may include continuing to deposit the bone grafting material at step 1818.

However, if the bone grafting material delivery device 100 needs to be adjusted, the method 1800 may include, at step 1820, adjusting the lock lever 154 so that the dilators 141 and/or the final dilator 142 may be adjusted to a new desired position. Once, the dilators 110 and/or the final dilator 142 is adjusted to the new desired position, the method 1800 may include relocking them into position using the lock lever 154 so that the bone grafting material may be deposited. However, in an embodiment, the method 1800 may include not relocking the dilators 141 and/or the final dilator 142, which may enable a physician to deposit bone grafting material to the deposit site while the physician is swiveling the dilators. Furthermore, it is important to note that the methods, devices, and kits described above may incorporate any of the functionality, components, and/or features described above or otherwise and are not intended to be limited to the description provided above.

Some of the steps of method 1800 can be completed without delivering bone grafting material or for that purpose, but to access a surgical area through a minimally invasive channel. Such an embodiment of the method 1800 can include the steps of determining a location on a body of a patient for creating a skin entry point, creating the skin entry point at the location on the body of the patient, positioning a needle in a bone of the patient via the skin entry point and attaching one or more dilators, such as sequence of a plurality of dilators in increasing size, to a portion of the needle by using a swivel assembly, where the dilators are configured to articulate from the needle in a plurality of degrees of freedom via the swivel assembly, and where a final dilator includes an opening at its distal end. The opening can be used to deliver biologics or for insertion of other instruments to access a bony area or deep tissue.

The illustrations of arrangements described herein are intended to provide a general understanding of the structure of various embodiments, and they are not intended to serve as a complete description of all the elements and features of apparatus and methods that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

We claim:

1. A bone grafting material delivery device, comprising:
   a needle having a cutting edge at a distal end of the needle, wherein the needle is configured to anchor to a location into a bone via a skin entry point created on a patient; and
   a dilator attachable to the needle using a swivel assembly, wherein the dilator is configured to articulate relative to the needle in a plurality of directions via the swivel assembly, wherein the dilator includes an opening at a distal end of the dilator for depositing bone grafting material onto or in at least one of the bone or a void;

wherein the swivel assembly includes a clamp, a dilator ring, a knob assembly, and a stud, wherein the swivel assembly is attached to the dilator by securing the dilator ring to the dilator using the knob assembly and stud, wherein the clamp of the swivel assembly is configured to receive a portion of the needle such that the needle is attached securely to the clamp of the swivel assembly.

2. The bone grafting material delivery device of claim 1, wherein the swivel assembly swivels the dilator with at least two degrees of freedom for depositing bone grafting material with the opening of the dilator.

3. The bone grafting material delivery device of claim 1, further comprising a trocar positioned within the dilator, wherein the trocar is configured to prevent tissue from entering the dilator.

4. The bone grafting material delivery device of claim 1, further comprising a plunger device configured to push to the bone grafting material through the opening of the dilator and onto at least one of the location of the bone and the void.

5. The bone grafting material delivery device of claim 1, wherein the bone grafting material includes at least one of an autograph, recycled bone, calcium phosphate, a synthetic, a biologic, or a combination thereof.

6. The bone grafting material delivery device of claim 1, further comprising a retractable burr configured to be connected to an inner grove of the dilator or freestanding, wherein the retractable burr is configured to decorticate the bone of the patient.

7. A bone grafting material delivery device, comprising:
a needle having a cutting edge at a distal end of the needle, wherein the needle is configured to anchor to a location into a bone via a skin entry point created on a patient; and
a dilator attachable to the needle using a swivel assembly, wherein the dilator is configured to articulate relative to the needle in a plurality of directions via the swivel assembly, wherein the dilator includes an opening at a distal end of the dilator for depositing bone grafting material onto or in at least one of the bone or a void;
wherein the dilator includes a sleeve configured to cover at least a portion of the opening of the dilator, wherein the sleeve is further configured to be adjusted to increase or decrease a size of the opening of the dilator.

8. A bone grafting material delivery device, comprising:
a needle having a cutting edge at a distal end of the needle, wherein the needle is configured to anchor to a location into a bone via a skin entry point created on a patient; and
a dilator attachable to the needle using a swivel assembly, wherein the dilator is configured to articulate relative to the needle in a plurality of directions via the swivel assembly, wherein the dilator includes an opening at a distal end of the dilator for depositing bone grafting material onto or in at least one of the bone or a void; and
a lock lever configured to lock the dilator into a fixed position.

9. A bone grafting material delivery device kit, the kit comprising:
a needle having a cutting edge;
a dilator configured to be attached to the needle via a swivel assembly, wherein the dilator is configured to articulate from the needle in a plurality of directions; the dilator configured to be attached to the needle via the swivel assembly, wherein the dilator includes an opening at a distal end of the dilator for depositing bone grafting material onto or in at least one of a bone or a void;
wherein the swivel assembly includes a clamp, a dilator ring, a knob assembly, and a stud, wherein the swivel assembly is attached to the dilator by securing the dilator ring to the dilator using the knob assembly and the stud, and wherein the clamp is configured to receive a portion of the needle such that the needle may be attached to the swivel assembly.

10. The bone grafting material delivery device kit of claim 9, further comprising a trocar configured to be positioned within the dilator, wherein the trocar is configured to prevent tissue from entering the dilator.

11. The grafting delivery material device kit of claim 9, further comprising a retractable burr configured to attach to the needle, wherein the retractable burr is configured to decorticate the bone.

* * * * *